US00PP36952P2

(12) United States Plant Patent
Kievit

(10) Patent No.: US PP36,952 P2
(45) Date of Patent: Sep. 9, 2025

(54) ***AGASTACHE* PLANT NAMED 'Balsumlora'**

(50) Latin Name: *Agastache hybrida*
Varietal Denomination: Balsumlora

(71) Applicant: Ball Horticultural Company, West Chicago, IL (US)

(72) Inventor: Christa Kievit, Hem (NL)

(73) Assignee: BALL HORTICULTURAL COMPANY, West Chicago, IL (US)

( * ) Notice: Subject to any disclaimer, the term of this patent is extended or adjusted under 35 U.S.C. 154(b) by 0 days.

(21) Appl. No.: 18/914,255

(22) Filed: Oct. 13, 2024

(51) Int. Cl.
*A01H 6/50* (2018.01)
*A01H 5/02* (2018.01)

(52) U.S. Cl.
USPC ..... Plt./399
CPC ..... *A01H 6/504* (2018.05)

(58) Field of Classification Search
USPC ..... Plt./399
CPC ..... A01H 6/50; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Agastache* plant named 'Balsumlora', characterized by its broadly upright to somewhat outwardly spreading and mounding plant habit; moderately vigorous growth habit; freely branching habit; dense and bushy appearance; medium green-colored leaves; freely flowering habit; relatively long and dense inflorescences with numerous deep pink-colored flowers; and good garden performance.

2 Drawing Sheets

Figure 1:
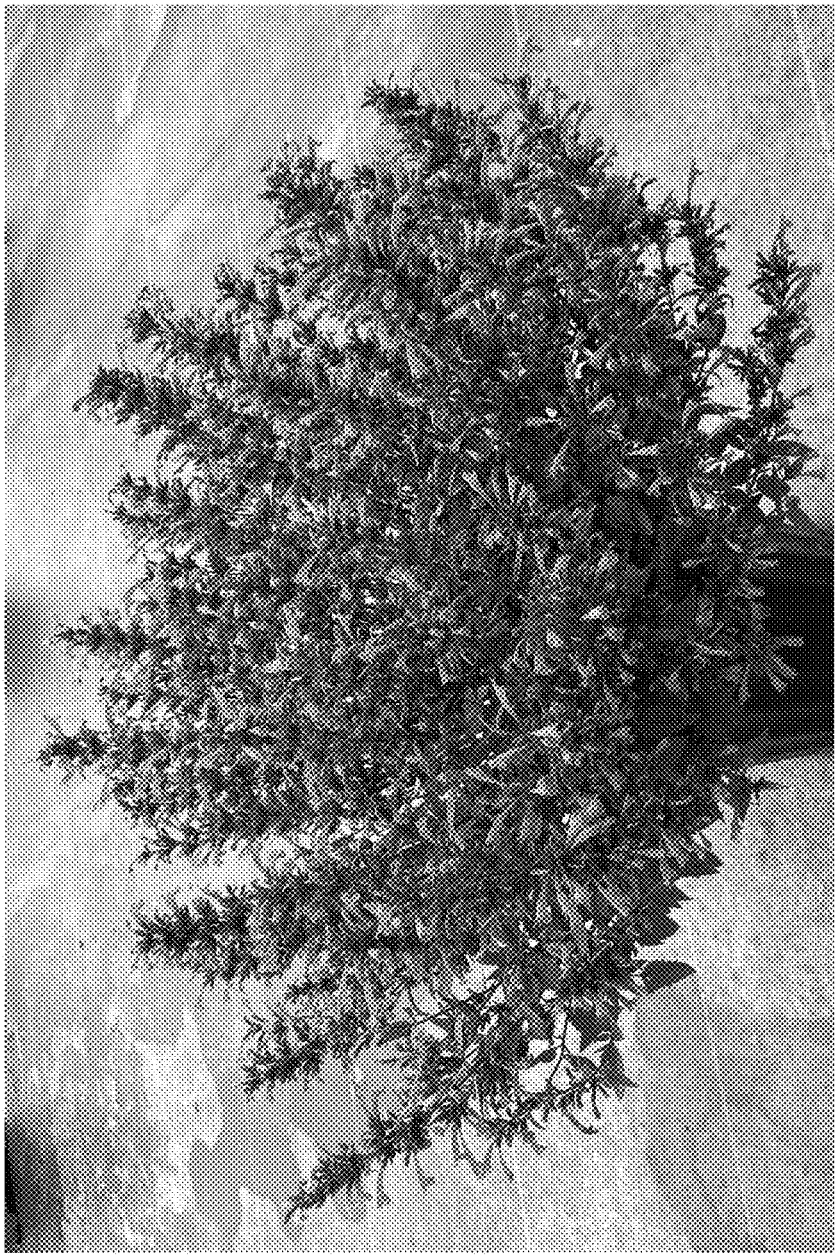

Botanical designation: *Agastache hybrida.*
Cultivar denomination: 'BALSUMLORA'.

BACKGROUND OF THE INVENTION

The present invention relates to a new and distinct cultivar of *Agastache* plant, botanically known as *Agastache hybrida,* commonly referred to as Giant Hyssop or Hummingbird Mint and hereinafter referred to by the name 'Balsumlora'.

The new *Agastache* plant is a product of a planned breeding program conducted by the Inventor in Hem, The Netherlands. The objective of the breeding program is to create new upright, mounded and dense *Agastache* plants that flower early and for a long period of time.

The new *Agastache* plant originated from a cross-pollination conducted by the Inventor in Hem, The Netherlands in June 2020 of a proprietary selection of *Agastache hybrida* identified as code number 20-112, not patented, as the female, or seed, parent with a proprietary selection of *Agastache hybrida* identified as code number 20-160, not patented, as the male, or pollen, parent. The new *Agastache* plant was discovered and selected by the Inventor as a single flowering plant from within the progeny of the stated cross-pollination in a controlled environment in Hem, The Netherlands in July 2021.

Asexual reproduction of the new cultivar by terminal stem cuttings in a controlled environment in Hem, The Netherlands and West Chicago, Illinois since July 2021 has shown that the unique features of this new *Agastache* plant are stable and reproduced true to type in successive generations.

SUMMARY OF THE INVENTION

Plants of the new *Agastache* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Balsumlora'. These characteristics in combination distinguish 'Balsumlora' as a new and distinct *Agastache* plant:

1. Broadly upright to somewhat outwardly spreading and mounding plant habit.
2. Moderately vigorous growth habit.
3. Freely branching habit; dense and bushy appearance.
4. Medium green-colored leaves.
5. Freely flowering habit.
6 Relatively long and dense inflorescences with numerous deep pink-colored flowers.
7. Good garden performance.

Plants of the new *Agastache* can be compared to plants of the female parent selection. In side-by-side comparisons, plants of the new *Agastache* differ primarily from plants of the female parent selection in flower color as plants of the new *Agastache* have deep pink-colored flowers whereas plants of the female parent selection have lighter pink-colored flowers. In addition, plants of the new *Agastache* are more mounding than plants of the female parent selection.

Plants of the new *Agastache* can be compared to plants of the male parent selection. In side-by-side comparisons, plants of the new *Agastache* differ primarily from plants of the male parent selection in flower color as plants of the new *Agastache* have deep pink-colored flowers whereas plants of the male parent selection have lighter pink-colored flowers. In addition, plants of the new *Agastache* flower earlier than plants of the male parent selection.

Plants of the new *Agastache* can be compared to plants of *Agastache hybrida* 'Kudos Coral', disclosed in U.S. Pat. No. 25,613. In side-by-side comparisons, plants of the new *Agastache* differ primarily from plants of 'Kudos Coral' in flower color as plants of the new *Agastache* have lighter-colored flowers than plants of 'Kudos Coral'. In addition plants of the new *Agastache* flower for a longer period of time and are denser and more uniform than plants of 'Kudos Coral'.

BRIEF DESCRIPTION OF THE PHOTOGRAPHS

The accompanying colored photographs illustrate the overall appearance of the new *Agastache* plant showing the colors as true as it is reasonably possible to obtain in colored reproductions of this type. Colors in the photographs may differ slightly from the color values cited in the detailed botanical description which accurately describe the actual colors of the new *Agastache* plant.

The photograph on the first sheet (FIG. 1) is a side perspective view of a typical flowering plant of 'Balsumlora' grown in a container.

Figure 2:
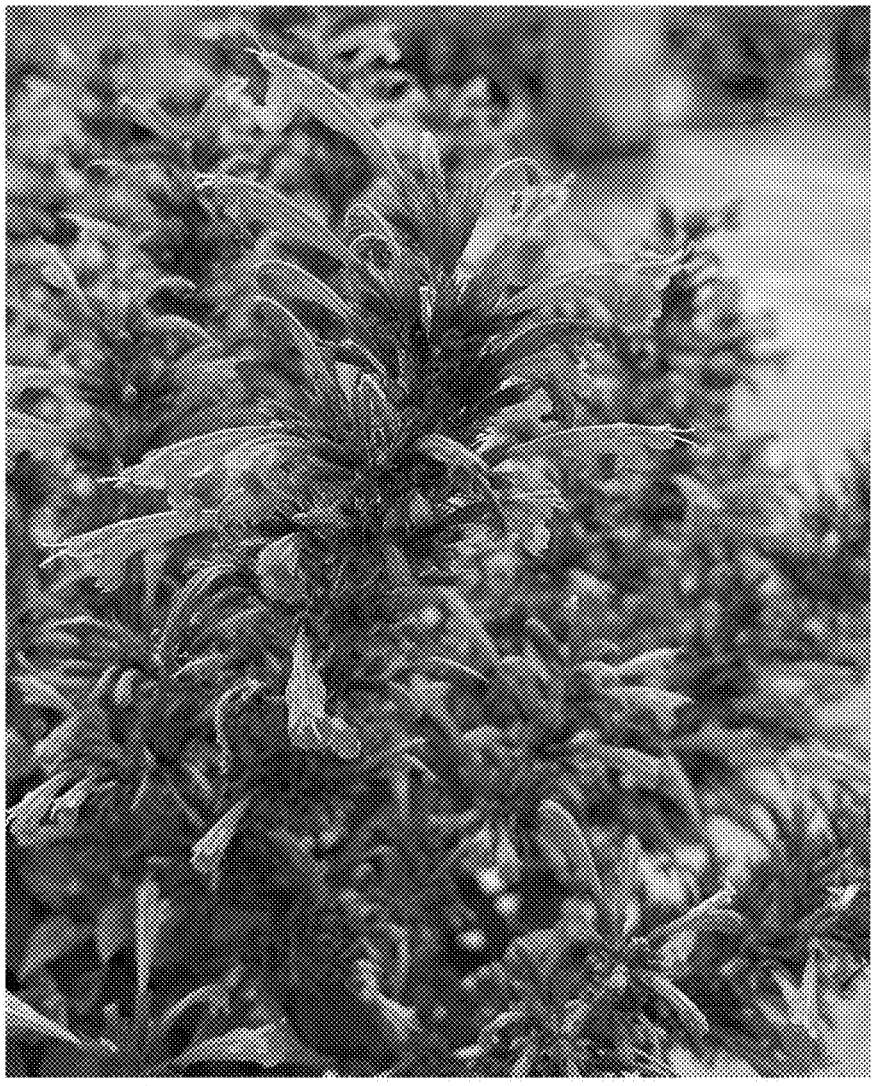

The photograph on the second sheet (FIG. 2) is a close-up view of a typical flowering plant of 'Balsumlora'.

DETAILED BOTANICAL DESCRIPTION

The aforementioned photographs and following observations and measurements describe 22-week old plants grown in 1.72-gallon containers. The plants were pinched two times prior to transplanting rooted young plants and grown in a polyethylene-covered greenhouse in West Chicago, Illinois for ten weeks prior to finishing the plants in an outdoor nursery in West Chicago, Illinois for an additional twelve weeks during the summer. Plants were grown under cultural practices typical of commercial *Agastache* production. In the following description, color references are made to The Royal Horticultural Society Colour Chart, 2015 Edition, except where general terms of ordinary dictionary significance are used.

Botanical classification: *Agastache hybrida* 'Balsumlora'.

Parentage:

- *Female, or seed, parent*.—Proprietary selection of *Agastache hybrida* identified as code number 20-112, not patented.
- *Male, or pollen, parent*.—Proprietary selection of *Agastache hybrida*identified as code number 20-160, not patented.

Propagation:

- *Type*.—By terminal stem cuttings.
- *Time to initiate roots*.—About ten to twelve days.
- *Time to produce a rooted young plant*.—About five to six weeks.
- *Root description*.—Fine to medium in thickness, fibrous; typically white to creamy white in color, actual color of the roots is dependent on substrate composition, water quality, fertilizer type and formulation, substrate temperature and physiological age of roots.
- *Rooting habit*.—Freely branching; dense.

Plant description:

- *Plant and growth habit*.—Herbaceous perennial typically grown as a container and garden plant; broadly upright to somewhat outwardly spreading and mounding plant habit; moderately vigorous growth habit; freely branching habit; dense and bushy appearance.
- *Commercial crop time*.—About ten to twelve weeks from planting rooted young plants are required to produce a finished flowering plant in a 15-cm container.
- *Branching habit*.—Freely basal branching with about six primary lateral branches, each primary lateral branch with potentially about eight secondary branches; pinching enhances lateral branch development.
- *Plant height*.—About 38 cm.
- *Plant width*.—About 53 cm.
- *Primary branch description*.—Length: About 11 cm. Diameter: About 3 mm. Internode length: About 4.5 cm. Shape: Quadrangular. Strength: Strong, flexible. Texture: Densely pubescent. Color, developing and developed: Close to 146A.

Leaf description:

- *Arrangement and quantity*.—Opposite and decussate; simple; about seven to ten leaves per lateral branch.
- *Length*.—About 1.5 cm.
- *Width*.—About 1.8 cm.
- *Shape*.—Ovate.
- *Apex*.—Broadly acute.
- *Base*.—Cordate.
- *Margin*.—Serrate with slightly rounded "teeth".
- *Texture, upper and lower surfaces*.—Densely pubescent.
- *Venation pattern*.—Pinnate.
- *Fragrance*.—Moderately fragrant; mint-like.
- *Color*.—Developing and fully expanded leaves, upper surface: Close to 137B to 137C; venation, close to 146A. Developing and fully expanded leaves, lower surface: Close to 147B; venation, close to 147C.
- *Petioles*.—Length: About 1.5 cm. Diameter: About 1.5 mm. Texture, upper and lower surfaces: Densely pubescent. Color, upper and lower surfaces: Close to 146C.

Flower description:

- *Flower arrangement and shape*.—Single bilabiate flowers arranged on mostly erect and relatively long and dense racemes; freely flowering habit with about 4 to 19 open flowers per inflorescence and at least 20 terminal and axillary inflorescences developing per plant during the flowering season; flowers face initially upright to mostly outwardly with development.
- *Fragrance*.—Moderately fragrant; mint-like.
- *Natural flowering season*.—Early flowering habit, depending on temperature, plants begin flowering about eight weeks after planting rooted young plants; long flowering period with plants continuously flowering from spring until the autumn in an outdoor environment in Illinois; depending on temperature, individual flowers last about six to seven days on the plant.
- *Flower buds*.—Length: About 1.3 cm. Diameter: About 3 mm. Shape: Clavate. Texture: Densely pubescent. Color: Close to 71A.
- *Inflorescence length* (*height*).—About 7 cm to 12 cm.
- *Inflorescence diameter*.—About 4 cm.
- *Flower size*.—About 4 mm by 10 mm.
- *Flower depth*.—About 1.8 cm.
- *Flower throat diameter*.—About 3 mm.
- *Flower tube length*.—About 8 mm.
- *Flower tube diameter, proximally*.—About 1 mm.

*Petals*.—Arrangement: Five petals; two fused upper petals (upper lip) with two lateral petals and one lower central petal (lower lip); petals fused towards the base. Upper petal lobes: Length: About 3 mm. Width: About 2 mm. Shape: Oblong. Apex: Obtuse. Base: Fused. Margin: Entire. Texture, upper surface: Smooth, glabrous. Texture, lower surface: Densely pubescent. Color: When developing and fully developed, upper surface: Close to 58C; venation, close to 58C; color does not change with subsequent development. When developing and fully developed, upper surface: Close to 47D; venation, close to 47D; color does not change with subsequent development. Lateral petal lobes: Length: About 1 mm. Width: About 2 mm. Shape: Orbicular. Apex: Obtuse. Base: Fused. Margin: Entire. Texture, upper surface: Smooth, glabrous. Texture, lower surface: Moderately pubescent. Color: When developing and fully developed, upper surface: Close to 58C; venation, close to 58C; color does not change with subsequent development. When developing and fully developed, upper surface: Close to 47D; venation, close to 47D; color does not change with subsequent development. Lower central petal lobe: Length: About 5 mm. Width: About 4 mm. Shape: Cup-shaped. Apex: Obtuse. Base: Fused. Margin: Crenate. Texture, upper surface: Smooth, glabrous. Texture, lower surface: Moderately pubescent. Color: When developing and fully developed, upper surface: Close to 58C; venation, close to 58C; color does not change with subsequent development. When developing and fully developed, upper surface: Close to 47D; venation, close to 47D; color does not change with subsequent development. Throat, texture: Smooth, glabrous. Throat color: Close to 10A. Tube, texture: Densely pubescent. Tube color: Close to 47D.

*Calyx*.—Arrangement: Five sepals fused to form a tubular calyx. Length: About 7 mm. Width: About 2 mm. Sepal length: About 7 mm. Sepal width: About 1 mm. Sepal shape: Roughly linear; fused. Sepal apex: Acute. Sepal margin, free part: Entire. Sepal texture, upper surface: Smooth, glabrous. Sepal texture, lower surface: Densely pubescent. Sepal color: When opening and fully opened, upper surface: Close to 140A to 140B. When opening and fully opened, lower surface: Close to NN77B.

*Peduncles*.—Length: About 4 cm. Diameter: About 2 mm. Texture: Densely pubescent. Color: Close to 146A.

*Pedicels*.—Length: About 1 mm to 2 mm. Diameter: About 1 mm. Strength: Strong, flexible. Aspect: At an acute angle to the peduncle axis. Texture: Densely pubescent. Color: Close to 140A to 140B with spots, close to 139A.

*Reproductive organs*.—Stamens: Quantity per flower: Four. Overall stamen length: About 2 cm. Filament length, free part: About 3 mm to 5 mm. Filament color: Close to N66B. Anther shape: Cleft. Anther length: About 1 mm. Anther color: Close to N79B. Pollen amount: Abundant. Pollen color: Close to NN155B. Pistils: Quantity per flower: One. Pistil length: About 2.1 cm. Stigma diameter: About 1.5 mm. Stigma shape: Bifurcate. Stigma color: Close to N80B. Style length: About 1.1 cm. Style color: Close to NN155D. Ovary color: Close to N145A.

*Seeds and fruits*.—To date, seed and fruit production has not been observed on plants of the new *Agastache*.

Pathogen & pest resistance: To date, plants of the new *Agastache* have not been noted to be resistant to pathogens and pests common to *Agastache* plants.

Garden performance: Plants of the new *Agastache* have exhibited good garden performance, that is, to tolerate rain, wind and to be hardy to USDA Hardiness Zone 7a.

It is claimed:

1. A new and distinct *Agastache* plant named 'Balsumlora' as herein illustrated and described.

* * * * *